(12) United States Patent
Chung

(10) Patent No.: US 7,276,072 B2
(45) Date of Patent: Oct. 2, 2007

(54) SKIN RESURFACING DEVICE

(76) Inventor: Tae-Jun Chung, 289-5, SungBok-Dong, Su Ji, Yongin City, Kyungki-Do (KR)

( * ) Notice: Subject to any disclaimer, the term of this patent is extended or adjusted under 35 U.S.C. 154(b) by 784 days.

(21) Appl. No.: 10/641,239

(22) Filed: Aug. 14, 2003

(65) Prior Publication Data

US 2005/0038448 A1    Feb. 17, 2005

(51) Int. Cl.
*A61B 17/50* (2006.01)

(52) U.S. Cl. ..................................... 606/131

(58) Field of Classification Search ............... 606/131, 606/133, 170, 180, 132, 167; 604/290, 289, 604/310, 311–316; 601/6, 7
See application file for complete search history.

(56) References Cited

U.S. PATENT DOCUMENTS

| | | | | |
|---|---|---|---|---|
| 5,207,234 A | * | 5/1993 | Rosso | 128/898 |
| 5,755,672 A | * | 5/1998 | Arai et al. | 600/547 |
| 6,019,749 A | * | 2/2000 | Fields et al. | 604/313 |
| 6,241,739 B1 | | 6/2001 | Wardron | 606/131 |
| 6,500,183 B1 | * | 12/2002 | Waldron | 606/131 |
| 6,629,983 B1 | * | 10/2003 | Ignon | 606/131 |
| 6,676,492 B2 | * | 1/2004 | Li | 451/65 |
| 2001/0023351 A1 | * | 9/2001 | Eilers et al. | 606/131 |
| 2003/0093089 A1 | * | 5/2003 | Greenberg | 606/131 |
| 2004/0254588 A1 | * | 12/2004 | Kim | 606/131 |

FOREIGN PATENT DOCUMENTS

| | | |
|---|---|---|
| KR | 20-0250506 | 10/2001 |
| KR | 20-0297355 | 11/2002 |

OTHER PUBLICATIONS

Brochure for Diamondtome Skin Resurfacing System by Altair Instruments, Date Unknown.

* cited by examiner

*Primary Examiner*—AnhTuan Nguyen
*Assistant Examiner*—Tuan Van Nguyen
(74) *Attorney, Agent, or Firm*—John K. Park; Park Law Firm

(57) ABSTRACT

A skin resurfacing device for peeling the outermost layer of the skin for renewing the skin surface and repairing skin damage including a housing, a skin sensor, and a skin treater. The skin treater consists of an abrasive tip, a first end, a transparent portion, a first filter, and a second end, all of which are detachable and replaceable. The skin treater is connected to a vacuum source by a tubular hose. The vacuum provides both closeness of contact between the abrasive tip and the user's skin and the suctioning of skin debris peeled off. The skin treater, especially the abrasive tip are made with common material and mass production process so that they are disposable and economic.

2 Claims, 5 Drawing Sheets

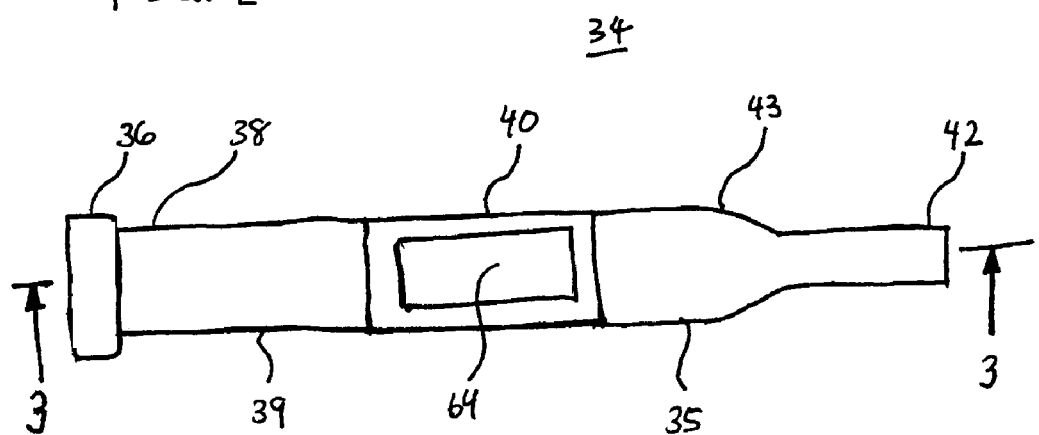
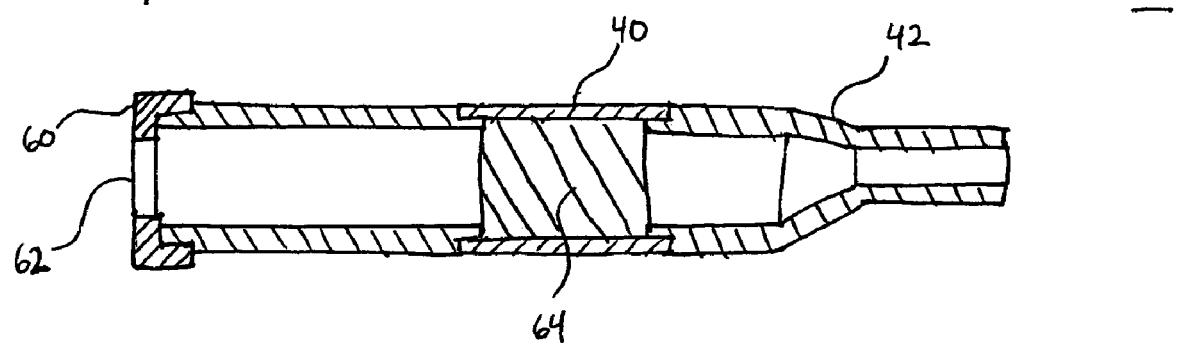

SKIN RESURFACING DEVICE

BACKGROUND OF THE INVENTION

The present invention relates to a skin resurfacing device. More particularly, this invention relates to a skin resurfacing device that peels the outermost layers of skin to provide a refreshed skin surface.

Dermabrasion is the process of removing skin blemishes or imperfections. By removing the outermost layer of skin, pigment lesions, skin discoloration, aging spots, lines, and other skin blemishes or imperfections can be treated and often repaired.

One technique in dermabrasion is to abrade the skin surface using compressed air, and a powdered, abrasive substance, typically microcrystals of quartz, metal, or aluminum oxide, then removing the abrasive substance and loosened skin tissue using a vacuum. The vacuum, through a treatment tool, collects skin debris after the crystals abrade the epidermis.

Another technique in dermabrasion is permanently attaching an abrasive material to the treatment tip, instead of a powdered substance. Often the permanently attached abrasive materials are diamonds, aluminum oxide, silicon carbide, silicon oxide, or metal nitrade. (U.S. Pat. Nos. 6,241,739 and 6,500,183). A disadvantage of this technique is when skin debris is held and remains between abrasive particles, it is very difficult to remove the debris completely. Remaining debris may cause serious medical problems such as bacteria infection. Remaining debris also degrade abrasion performance. Disadvantages of the prior art include the need for these techniques to be typically administered in medical facilities and requiring commercial means for sterilization and cleaning of the abrasive tip. Thus, these techniques of dermabrasion are often very expensive.

SUMMARY OF THE INVENTION

The present invention contrives to solve the disadvantage of the prior art.

An objective of the invention is to provide a skin resurfacing device designed for both domestic and professional use that is inexpensive and simple to use. Another objective of the invention is to provide a disposable and replaceable skin resurfacing device so there is either no need or minimum need to sanitize or clean the abrasive tip that contacts and peels the skin. Yet another objective of the invention is to provide a double filtering system that is visible to the user to insure proper functioning of the skin resurfacing device.

To achieve the above objectives, a device for skin resurfacing comprises a skin treater, and a vacuum source connected to the skin treater. The skin treater comprises a hollow tube having a first end, a second end, an abrasive tip detachably fixed on the first end, a first filter that is provided inside the tube between the first end and the second end where the vacuum source is connected to the second end. The hollow tube of the skin treater has a transparent portion so that the filter is visible outside. The abrasive tip has abrasive particles. In another embodiment of the skin treater, the parts are not detachable, but the entire skin treater is disposable.

The abrasive particles of the abrasive tip consist of aluminum oxide crystals, silicon carbide crystals, or silicon oxide crystals having a predetermined range of size from about sixty (60) μ to about one hundred fifty (150) μ. The abrasive tip is made by pressure molding and heat treating the abrasive particles. The abrasive tip has a flat annular portion that contacts the skin of a user, and wherein a suction hole is provided in the annular portion through which air is sucked. The abrasive tip is coated with liquid ceramic material that is colored with different colors according to the different size of abrasive crystals. In another embodiment of the abrasive tip, the abrasive tip has a roller that protrudes from the flat annular portion so the roller contacts and rolls on the skin of the user.

The skin resurfacing device has a skin sensor that measures the oiliness of the skin of a user. The intensity of the vacuum provided by the vacuum source is automatically controlled according to the measured oiliness by the skin sensor or manually controlled by the user. The skin resurfacing device has a timer that controls the operation time of the device.

There is also a second filter between the skin treater and the vacuum source that includes a container that with an open end, a lid that plugs the open end, an inlet pipe passing through the lid, an outlet pipe passing through the lid, and a filter element that is fixed to the outlet pipe. The container is detachable from the lid.

The advantages of the present invention are: (1) a skin resurfacing device of the present invention is suitable for mass production at low cost; (2) a skin resurfacing device that is inexpensive in relation to other skin resurfacing devices; (3) the skin resurfacing device that is made for both personal and professional use; (4) the skin resurfacing device that has a double filtering system filters the skin debris with greater efficiency; (5) a skin treater of the skin resurfacing device that has detachable parts for ease of disposal, replacement, and cleanliness; and (6) a skin treater that provides a replaceable and disposable abrasive tip.

Although the present invention is briefly summarized, the fuller understanding of the invention can be obtained by the following drawings, detailed description and appended claims.

DESCRIPTION OF THE FIGURES

These and other features, aspects and advantages of the present invention will become better understood with reference to the accompanying drawings, wherein:

FIG. 2 is an elevation view of a skin treater;

FIG. 3 is a cross-sectional view taken along the line 3-3 of FIG. 2;

DETAILED DESCRIPTION OF THE INVENTION

Figure 1:
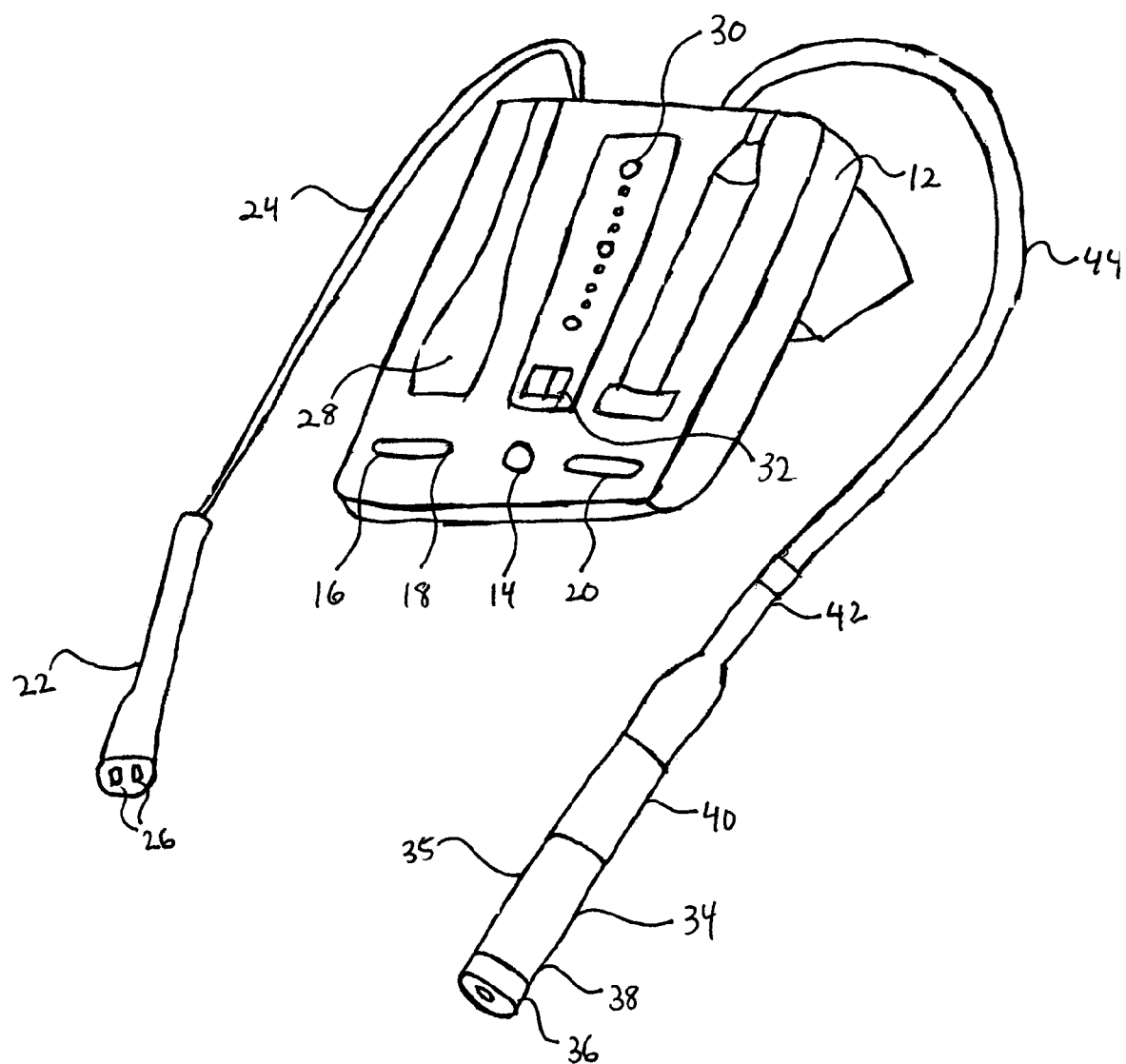
FIG. 1 is a perspective view of a skin resurfacing device according to the present invention.

FIG. 1 shows a skin resurfacing device 10 which has a housing 12, a skin sensor 22, and a skin treater 34. The housing 12 comprises an ON/OFF switch 14, a skin sensor starting button 16 to measure the level of skin oiliness, a skin peeling start button 18 to begin the skin peeling process, and a pressure controller button 20 for controlling the intensity of the peeling pressure and vacuum pressure. The skin sensor 22 is connected to the housing 12 by an electrical wire 24. Skin sensor electrodes 26 that measure the oiliness of the skin are provided on the skin sensor 22 on the opposite end of the electrical wire 24. The skin sensor 22 can be placed in the skin sensor slot 28 when the skin sensor 22 is not in use. The skin resurfacing device 10 adjusts the pressure applied in the peeling process based on the oiliness of skin measured by the skin sensor 22. The intensity of the peeling pressure and vacuum pressure is also controllable with the pressure controller button 20 and the amount of intensity is indicated by the pressure indicator 30. The LED timer 32 times each individual skin resurfacing session. When the device 10 is turned on, the timer is reset for a time that is usually from 15 to 20 minutes.

A skin treater 34 has a hollow tube 35 having a first end 38, a second end 42, an abrasive tip 36 detachably fixed on the first end 38, and a first filter 64 provided between the first end 38 and the second end 42. The skin treater 34 is connected to a vacuum source inside the housing 12 by a tubular hose 44 at the second end 42. The strength of vacuum is displayed by the LED pressure indicator 30. The user can manually adjust the vacuum strength that has been automatically set by the device 10. The contact strength of the skin treater 34 on the skin of the user follows the vacuum strength. When the vacuum is strong, the abrasive tip 36 adhere to the skin more tight. After the timer is off, the device continues to suck air for about 10 seconds so that debris within the skin treater 34 is removed.

FIG. 2 is a front elevation view of the skin treater 34. The hollow tube 35 includes an abrasive tip 36, a first tube 39, a transparent portion 40, and a second tube 43. The first filter 34 is located inside the transparent portion 40. The abrasive tip 36, first tube 39, transparent portion 40, first filter 64, and second tube 43 are all detachable for ease of cleaning and replacement. The transparent portion 40 of the skin treater 34 allows the first filter 40 to be visible to the user. Thus, the user is able to see and confirm that the skin resurfacing device 10 is functioning properly. The transparent portion 40 that allows visibility of the first filter 40 also serves to inform the user when the skin treater 34 and all the comprising parts need replacement, either individually or as a whole.

As shown in FIG. 3 the abrasive tip 36 has a flat annular portion 60 that contacts the skin of the user. The abrasive tip 36 also has a suction hole 62 in the annular portion 60 where air is suctioned in causing skin particles peeled by the abrasive tip 36 to be suctioned in as well. Once the abrasive tip 36, which is made of aluminum oxide or silica oxide crystals between the predetermined range of sixty (60) μ to about one hundred fifty (150) μ, peels the outer layer of the skin, it is suctioned through the suction hole 62 as the skin treater 34 is moved along the skin in a direction consistent with the muscles of the skin. The variance in range of the crystals on the abrasive tip produce different levels of abrasion, with the larger particles peeling skin more rapidly. The abrasive tips are color-coordinated according to the predetermined range and are easily detachable and replaceable. The abrasive tip is made by pressure molding a mixture of aluminum oxide powder, silicon oxide ($SiO_2$), and $Fe_2O_3$, etc. and heat treating the molded mixture at about 2000 degree Celsius to solidify the mixture. The solidified mixture has a little porosity. However, it is desirable to remove any porosity in order not to degrade suction performance of the skin treater. Liquid ceramic material is coated on the surface of the abrasive tip to seal pores. The liquid ceramic material is colored with a different color for a different size of abrasive crystals. Thus the color of the coating indicates abrasive particle size. Skin resurfacing operation is enhanced by choosing different abrasive size for different skin conditions.

Sanitary concerns, such as skin debris lodged in and between the crystals are reduced or eliminated because the abrasive tip 36 is very easily changed. Particles and skin debris picked up by the vacuum through the suction hole 62 pass along the first tube 39 to the transparent portion 40 that contains the first filter 64. The first filter 40 filters the debris so mostly air is passed to the second tube 43.

Figure 4:
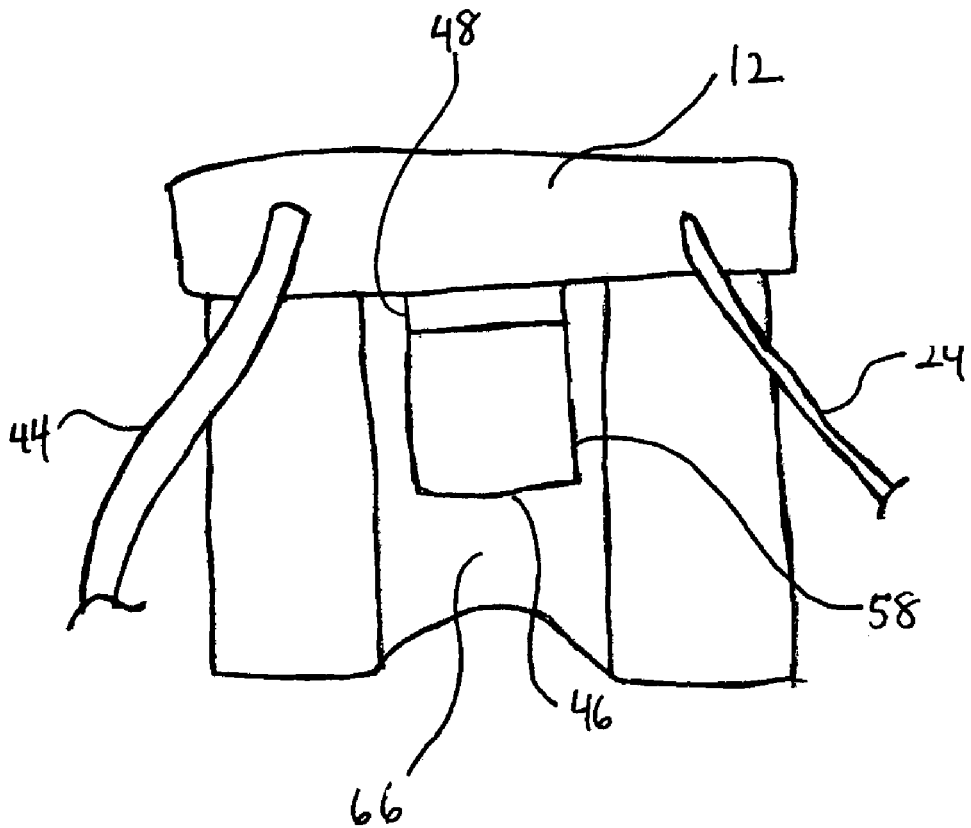
FIG. 4 is a rear view of the skin resurfacing device.

FIG. 4 shows the back of the housing 12 where the electrical wire 24 and the tubular hose 44 are connected. A rear recess 66 is provided in the back of the housing 12 to hold the second filter 46. The second filter 46 is provided between the skin treater 34 and the vacuum source.

Figure 5:
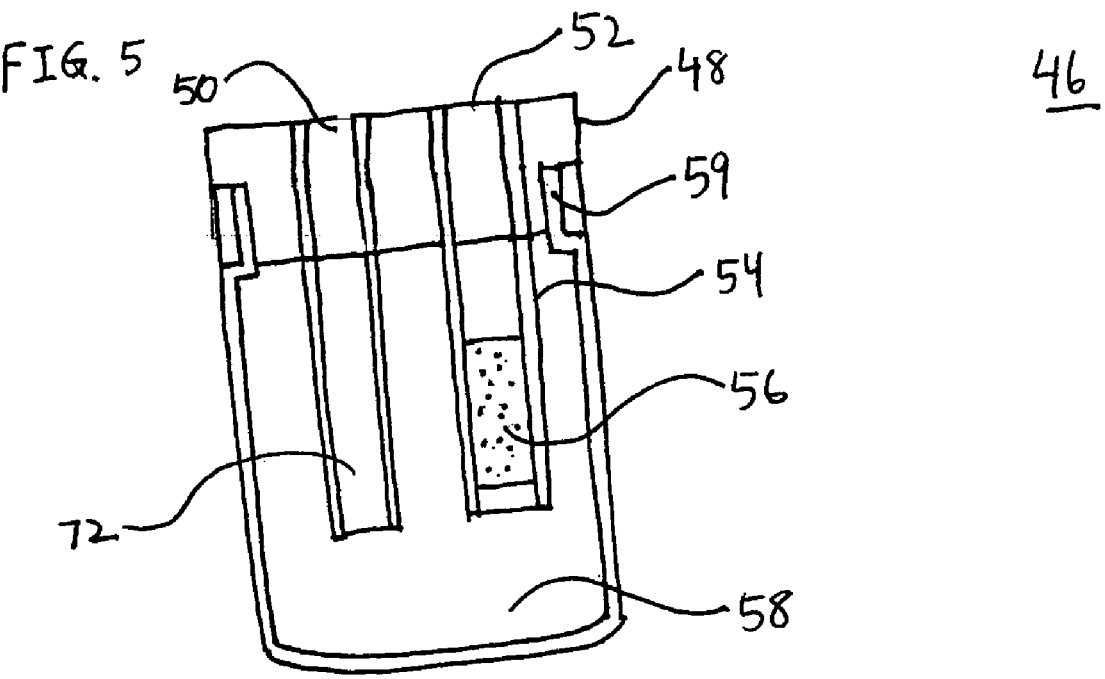
FIG. 5 is a cross-sectional view of a second filter.

FIG. 5 shows the second filter 46 comprising a lid 48 that is fixed to the housing 12. The lid 48 contains two openings, a first opening 50 and a second opening 52. An inlet hose 72 runs through the first opening 50. An outlet tube 54 from the vacuum source runs through the second opening 52. The outlet tube 54 contains a filter element 56 that acts as a second line of filtering after the first filter 64. A container 58 with an open end 59 is provided. The open end 59 is plugged by the lid 48. The container 58 is detachably attached to the lid 48 and encloses the inlet hose 72 and the outlet tube 54. Any remaining debris and mostly air pass from the second tube 43 are routed into the first opening 50 of the lid 48 through the inlet tube 72 and then falls to the bottom of the container 58 due to gravity. The vacuum source provides a vacuuming effect that collects skin debris by suctioning skin peeled by the abrasive tip 36. The vacuum source 68 also increases the closeness of contact between the abrasive tip 36 and the user's skin due to the flow of air through the skin treater 34. The outlet pipe 54 powered by the vacuum source picks up the smaller debris. Any debris that is picked up by the outlet pipe 54 is filtered by the filter element 56 so only air flows past the filter element 56.

Figure 6:
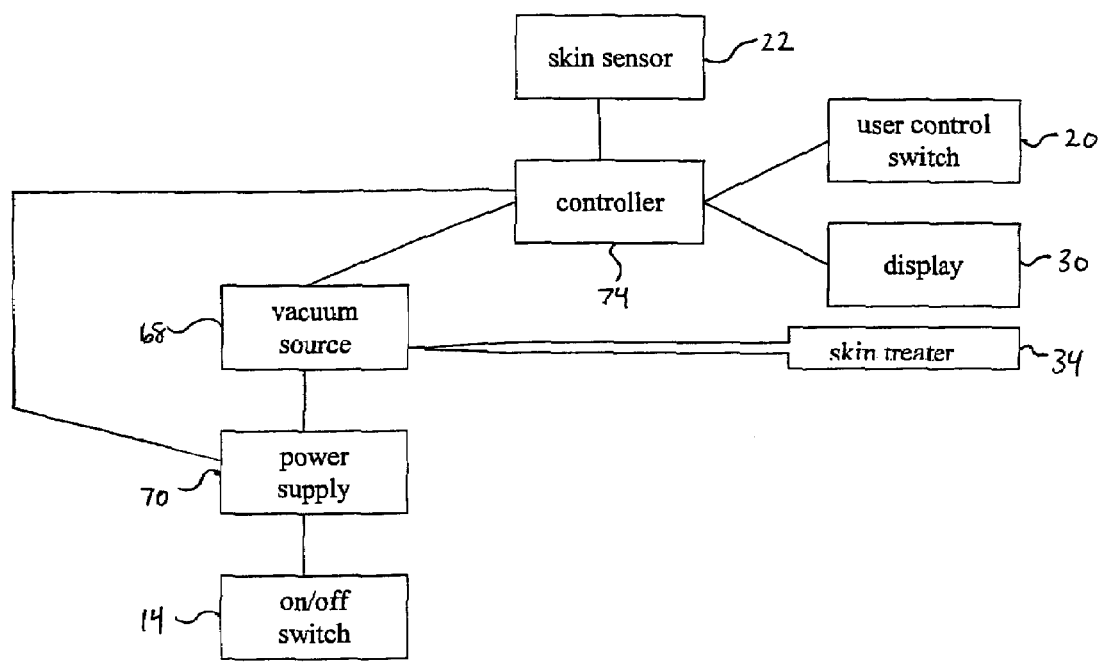
FIG. 6 is a block diagram of the skin resurfacing process.

FIG. 6 shows a block diagram of the skin resurfacing process. To operate the skin resurfacing device 10, the ON/OFF switch 14 activates the power supply 70. The skin sensor 22, with skin sensor electrodes 26 at the end, measures the oiliness of the user's skin. The controller 74 adjusts vacuum pressure of the skin peeling process. The pressure is automatically set at a constant level by the controller based on the measurement of oiliness displayed on the pressure indicator 20. The user is also able to adjust the pressure with the pressure controller button 20 according to the desired pressure at either constant or variable levels. The skin treated 34 is connected to the vacuum source 68 that is also adjusted by the controller 74. The skin treater 34 is disposable.

Figure 7:
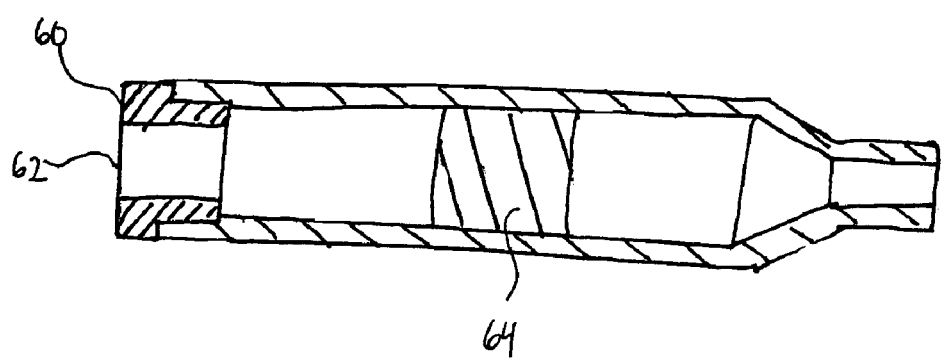
FIG. 7 is a cross-sectional view of another embodiment of a skin treater and abrasive tip.

FIG. 7 shows a skin treater 34 having an abrasive tip 36 having a different shape. Also the skin treater 34 has a transparent hollow tube 35.

Figure 8:
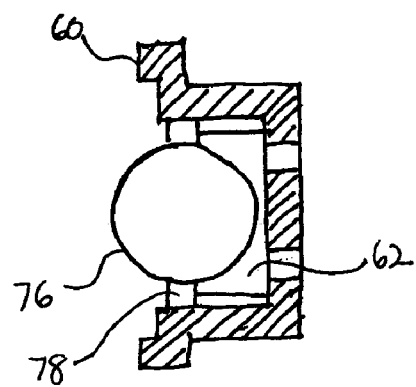
FIG. 8 is a cross-sectional view of the an abrasive tip with a roller.

FIG. 8 shows an abrasive tip that is similar to the abrasive tip 36 but further includes a roller 76 that protrudes from the flat annular portion so that the roller 76 contacts and rolls on the skin of a user. The roller 76 is rotationally attached to the wall of the abrasive tip 36 with a rotation axis 78. The roller 76 has a role of pressing the portion of the skin that is resurfaced by the skin resurfacing device 10.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:
1. A skin resurfacing device comprising:
a housing; a skin treater;

a vacuum source located within the housing and connected to the skin treater;

a skin sensor that is adapted to measure the oiliness of the skin of a user and the skin sensor is connected to the housing; and wherein the skin treater comprises a hollow tube having a first end, a second end, an abrasive tip detachably fixed on the first end, a first filter that is provided inside the tube between the first end and the second end, wherein the abrasive tip comprises abrasive particles, and wherein the vacuum source is connected to the second end, wherein the intensity of the vacuum provided by the vacuum source is controlled according to the measured oiliness by the skin sensor.

2. The skin resurfacing device of claim 1 wherein a user can adjust the intensity of the vacuum.

* * * * *